United States Patent [19]
Hansen et al.

[11] Patent Number: 5,741,270
[45] Date of Patent: Apr. 21, 1998

[54] MANUAL ACTUATOR FOR A CATHETER SYSTEM FOR TREATING A VASCULAR OCCLUSION

[75] Inventors: Gerald Hansen, Newark; E. Richard Hill, III, Berkely; Charles Milo, Union City, all of Calif.

[73] Assignee: LuMend, Inc., Menlo Park, Calif.

[21] Appl. No.: 808,092

[22] Filed: Feb. 28, 1997

[51] Int. Cl.⁶ .................................................. A61F 11/00
[52] U.S. Cl. .......................... 606/108; 606/174; 606/205; 606/207; 606/208
[58] Field of Search .................................. 606/174, 108, 606/205, 207, 208; 604/164

[56] References Cited

U.S. PATENT DOCUMENTS

| | | |
|---|---|---|
| 3,640,270 | 2/1972 | Hoffman . |
| 4,355,643 | 10/1982 | Laughlin et al. . |
| 4,541,433 | 9/1985 | Baudino . |
| 4,698,057 | 10/1987 | Joishy . |
| 5,102,390 | 4/1992 | Crittenden et al. . |
| 5,193,546 | 3/1993 | Shaknovich . |
| 5,282,817 | 2/1994 | Hoogeboom et al. ................... 606/174 |
| 5,308,357 | 5/1994 | Lichtman ................................. 606/205 |
| 5,321,501 | 6/1994 | Swanson et al. . |
| 5,336,252 | 8/1994 | Cohen . |
| 5,355,871 | 10/1994 | Hurley et al. ............................ 606/205 |
| 5,383,467 | 1/1995 | Auer et al. . |
| 5,423,846 | 6/1995 | Fischell . |
| 5,439,000 | 8/1995 | Gunderson et al. . |
| 5,459,570 | 10/1995 | Swanson et al. . |
| 5,484,412 | 1/1996 | Pierpont . |
| 5,507,295 | 4/1996 | Skidmore . |

*Primary Examiner*—Michael Buiz
*Assistant Examiner*—Daphna Shai
*Attorney, Agent, or Firm*—Peninsula IP Group; Douglas A. Chaikin, Esq.

[57] ABSTRACT

Disclosed herein is manual actuator for retracting and advancing a therapeutic working element of an intravascular catheter system via an actuation shaft or one or more pulling wires. The manual actuator includes a hollow cylindrical bracing member having an open proximal end and a distal end, and a hollow cylindrical retracting member, the retracting member being slidable, in a telescoping fashion, into the open proximal end of the bracing member. An actuation shaft is secured near to the proximal end of the retracting member and the distal end of the actuation shaft is secured to the therapeutic working element. Alternatively, at least one pulling wire is secured proximal to the proximal end of the retracting member. The distal end of the pulling wire is secured to the therapeutic working element. At least one resilient connecting member has a proximal end attached proximate the proximal end of the retracting member, and a distal end attached proximate the distal end of the bracing member. When a manually applied external force is applied by the physician to the resilient connecting members, the resilient connecting members urge the retracting member in a proximal direction with respect to the bracing member, and retracting the actuation shaft to thereby operate the working element of the catheter system. Alternatively, the retracting member is urged in the proximal direction by the manually applied external force and the pulling wires transmit this force to the therapeutic working element.

34 Claims, 3 Drawing Sheets

MANUAL ACTUATOR FOR A CATHETER SYSTEM FOR TREATING A VASCULAR OCCLUSION

BACKGROUND OF THE INVENTION

1. Field of the Invention

This invention relates generally to medical devices and especially to intravascular catheters designed to operate with respect to occlusions within a blood vessel. More particularly, this invention relates to manual actuators for intravascular catheters equipped with actuation shafts whose therapeutic working elements require a slow and selectively applied reciprocal motion for fracturing or otherwise treating an occlusion.

2. Background

Medical science has long sought effective treatments for disease conditions involving stenosis (narrowing or obstruction) of the lumen (interior passage of the artery) of an artery. This condition, known generally as an occlusion, is found in patients suffering from atherosclerosis (accumulation of fibrous, fatty or calcified tissue in the arteries). An occlusion can manifest itself as hypertension (high blood pressure), ischemia (deficiency of circulation), angina (chest pain), myocardial infarction (heart attack), stroke, or death. An occlusion may be partial or total, may be soft and pliable or hard and calcified, and may be found at a great variety of sites in the arterial system including the aorta, the coronary and carotid arteries, and peripheral arteries.

Of particular interest to cardiac medicine are the often disabling or fatal occlusions occurring in the coronary arteries (arteries supplying the heart). Traditionally, coronary artery occlusions have been treated by performing coronary bypass surgery, in which a segment of the patient's saphenous vein is taken from the patient's leg and is grafted onto the affected artery at points proximal (upstream) and distal (downstream) to the occluded segment. The bypass often provides dramatic relief. However, it entails dangerous open chest surgery and a long, painful, costly convalescence in the hospital. Moreover, with the passage of time, the bypass patient's saphenous vein graft can also become occluded. If the patient has another saphenous vein, a second bypass procedure may be performed, once again entailing open chest surgery and prolonged hospitalization. Thereafter, if the underlying atherosclerotic disease process is not controlled, the prognosis is dismal.

Newer, minimally invasive procedures are now preferred in the treatment of arterial occlusions. These procedures use a catheter, a long, thin, highly flexible device which is introduced into a major artery through a small arterial puncture made in the groin, upper arm, or neck and is advanced and steered into the site of the stenosis. At the distal end of the catheter, a great variety of miniature devices have been developed for operating upon the stenosed artery.

The more popular minimally invasive procedures include percutaneous transluminal coronary angioplasty (PTCA), directional coronary atherectomy (DCA), and stenting. PTCA employs a balloon to mechanically dilate the stenosis. In PTCA, a steerable guidewire is introduced and advanced under fluoroscopic observation into the stenosed artery and past the stenosis. Next, a balloon-tipped catheter is advanced over the guidewire until it is positioned across the stenosed segment. The balloon is then inflated, separating or fracturing the atheroma (stenosed tissue). The hoped for outcome is that, over time, the lumen will stay open.

In directional coronary atherectomy, a catheter containing a cutter housed in its distal end is advanced over the guidewire into the stenosed segment. The housing is urged against the atheroma by the inflation of a balloon, so that part of the atheroma intrudes through a window in the side of the housing. Under fluoroscopic observation, the cutter is used to shave away the atheroma. The shavings are collected in the nosecone of the housing and withdrawn along with the catheter.

Stenting is a procedure in which a wire framework, known as a stent, is compressed and delivered via a balloon catheter. The stent is positioned across the stenosed segment of the artery. The balloon is inflated, dilating the stent and forcing the stent against the artery wall. The hoped-for outcome is that the stent will hold the arterial lumen open for a prolonged period. Frequently, a stent is placed in an artery immediately following PTCA or DCA.

It must be noted, however, that the aforementioned catheters are "over-the-wire catheters." These catheters depend on the guidewire, which typically has a tiny bent portion at its distal end for steering. Over-the-wire catheters cannot be positioned adjacent the stenosis until the guidewire has been advanced across the stenosed arterial segment. Thus, where the occlusion is too severe to be crossed by a guidewire or where there is not enough room for the balloon, cutter, or stent delivery catheter, neither PTCA nor DCA nor stenting can be done. Unfortunately, the occlusion often contains extremely hard, calcified tissue and presents an impenetrable barrier to the guidewire. Even a less than total occlusion may contain complex structures which divert or trap the steering end of the guidewire. Thus, the guidewire might not completely cross the occlusion, but become diverted into the subintimal space between the intima and the atheroma or become buried in the atheroma. In either case, the guidewire cannot be positioned across the stenosis to guide a balloon or cutting element. In such cases, bypass surgery may be necessary with the associated cost, risks, and recovery period.

Thus, in patients suffering from severe or total arterial occlusion, it is preferable to do what has been difficult or impossible in the past: to open the severely or totally occluded artery itself, rather than by performing a bypass. If a guidewire and working catheter can be passed through or around the atheroma, the severe or total occlusion can be treated by PTCA, DCA, stenting, site-specific drug delivery or a combination of these proven therapies.

It would be advantageous to find and open a path of low resistance, either through or around the atheroma. Of course, this must be done without perforating arterial wall. Clearly, the serious consequences of penetrating the arterial wall must be avoided at all costs. The physician will not use a system which would be unsafe and no patient would want a physician to use such a system. Therefore, any solution to the problem of finding and creating an opening through or around the atheroma must be safe and in many instances include a system of guidance for the device that would find and open such an occlusion.

There has been a long felt need to provide a reliable system of guidance for such a device. As understood by those in the art, the device must travel a crisscrossing, often maze-like structure before it even gets to the occlusion. Then the occlusion itself is often a maze like structure. Attempting to cross such an occlusion without reliable guidance is dangerous. For example, it is easy to dissect the tissues of the arterial wall instead of the occlusion, thereby creating a false lumen and possibly perforating the artery. If blood escapes the artery and accumulates in the pericardial space, it will compress the heart, requiring emergency intervention to avert heart failure and death.

One guidance system which has been used in conjunction with coronary catheterization is biplane fluoroscopy, wherein the interventionist observes two flat real-time x-ray images acquired from different angles. Biplane fluoroscopy, however, is unreliable, costly, and slow. Delay is unacceptable, for it contributes to trauma and stress and creates opportunities for complications and failures of technique.

Recently, promising optical systems have been disclosed for imaging an occlusion through a catheter placed in the artery. One such system is Optical Coherence Tomography (OCT). In OCT, a beam of light carried by an optical fiber illuminates the artery interior. In a radar-like manner, light reflected back into the fiber from features inside the artery is correlated with the emitted light to capture the depth as well as the angular separation of those features. The features are displayed graphically in two or three dimensions through the use of a suitably programmed computer.

The beam in OCT is swept by mechanical rotation or movement of optical components in the catheter, or by optical switching devices which select one of several fibers through which to perform measurements. The rotation is encoded, or the switching pattern recorded, for reconstructing angular information about the artery interior. For example, a beam splitter may be placed between the light source and the catheter fiber to produce a reference beam which is directed to a reflector at a known distance. The catheter beam and the reference beam are recombined as they return. When the paths traveled by the two beams are of equal optical length, interference fringes are observable in the combined beam. Since the lengths of the reference path and the catheter fiber are known, the distance from the fiber end to a particular reflective feature within the artery can be inferred. In OCT and related methods, signals may also be impressed upon the light beam to facilitate the measurement of distance or the detection of motion of objects relative to the fiber end. By means of OCT or other similar optical methods, imaging capability can be incorporated into an intravascular catheter or guidewire.

However, while superior imagery alone is of diagnostic interest, effective intervention for severe occlusive arterial disease is what is truly desired. Even with improved guidance, there persists a long felt need for working elements which are capable of opening a path through or around an arterial occlusion at low risk of perforating the artery. What is needed is an intravascular catheter system for the effective treatment of the severely occluded artery and, in particular, the totally occluded artery. What is especially needed is a therapeutic working element which allows the physician to mechanically fracture an occlusion or to separate the occlusion from the intimal surface, but which is operable in a manner unlikely to perforate the adventitia.

However, effective intervention requires a precise control over the operation of the therapeutic working element. In some applications, it is desired to rotate a cutter within a catheter working element at a high rate of speed, to thereby envaginate the occlusive material, cut it and store it in a nosecone of the catheter. Other applications require a slow reciprocal motion of the catheter actuation shaft, to allow a therapeutic working end to mechanically fracture or to otherwise treat the occlusion. Moreover, this slow reciprocal motion must be a controlled motion, and the force applied to the catheter actuation shaft must be selectively controllable by the cardiac interventionist. There has been a long felt need for a manually controllable actuator for operating a working element of an intravascular catheter device. What is needed is a manual actuator for therapeutic working elements of catheter devices, that allows the intravascular catheter operator to manually and selectively control the reciprocal movement of the actuation shaft connected to the working elements of catheters.

SUMMARY OF THE INVENTION

It is an object of this invention to provide an actuator for a therapeutic working element of an intravascular catheter system.

It is an additional object of this invention to provide such an assembly wherein the assembly includes a manual actuator for manually and selectively retracting and advancing a therapeutic working element of an intravascular catheter system. In accordance with the above objects and those that will be mentioned and will become apparent below, the manual actuator for retracting and advancing a therapeutic working element of an intravascular catheter system in accordance with this invention comprises:

- a hollow cylindrical bracing member including an open proximal end and a distal end;
- a hollow cylindrical retracting member, the retracting member being slidable into the open proximal end of the bracing member, the retracting member having a proximal end;
- an actuation shaft, a proximal end of the actuation shaft being secured to the proximal end of the retracting member, a distal end of the actuation shaft being secured to the therapeutic working element, and
- at least one resilient connecting member having a proximal end attached proximate the proximal end of the retracting member, and a distal end attached proximate the distal end of the bracing member,
- whereby a manually applied external force applied to the at least one resilient connecting member urges the retracting member in a proximal direction with respect to the bracing member, thereby retracting the actuation shaft and operating the working element of the catheter system.

In one exemplary embodiment of the invention, the manual actuator, further comprises a pair of bracing member mounting pins secured to the bracing member at a position proximate the distal end of the bracing member and projecting radially from the bracing member, and a pair of retracting member mounting pins secured to the retracting member at a position proximate the proximate end of the retracting member and projecting radially from the retracting member. The proximal end of each of the at least one connecting member is pivotally attached to a corresponding pin of the pair of retracting member mounting pins and the distal end of each of the at least one connecting member is pivotally attached to a corresponding pin of the pair of bracing member mounting pins.

In another exemplary embodiment of the present invention, the pair of bracing member mounting pins and the pair of retracting member mounting pins are unitarily and integrally formed.

In yet another exemplary embodiment, the proximal end of the hollow cylindrical retracting member is fitted with a proximal hub having an axial through bore for accommodating at least the actuation shaft along at least a portion of the longitudinal axis of the proximal hub. Alternatively, the cylindrical base portion and the endcap include an actuating shaft axial through bore dimensioned to accommodate at least an actuation shaft of the catheter system. Alternatively still, the cylindrical base portion includes an actuating shaft axial through bore dimensioned to accommodate at least the actuation shaft, and the endcap includes a guidewire axial through bore dimensioned to accommodate a guidewire of the catheter system, the guidewire axial through bore being aligned with the actuating shaft axial through bore.

In this exemplary embodiment, the proximal end of the actuation shaft is anchored within the proximal hub. The proximate hub has a cylindrical base portion and an integral endcap, the proximal end of the actuation shaft being anchored within the integral endcap.

It is an advantage of this exemplary embodiment that externally applied manual pressure on the connecting members causes a corresponding retraction of the retracting member, which, in turn, retracts the actuating shaft. The retraction of the actuating shaft causes at least a portion of the therapeutic working member to also retract, thereby operating the working member.

In another exemplary embodiment of the present invention, each of the at least one resilient connecting member is made of a thin strip of resilient material which regains its shape after being deformed. It is an advantage of this exemplary embodiment that manual squeezing pressure applied to the connecting members by a physician will cause deformation of the resilient members, which will then regain their original shape after the physician has released the squeezing pressure, thereby allowing the physician to repeatedly squeeze and release the resilient connecting members and operate the therapeutic working member of the intravascular catheter device.

In another exemplary embodiment, the distal end of the hollow cylindrical bracing member is fitted with a distal hub having an axial through bore for accommodating at least the actuation shaft.

In yet another exemplary embodiment, a manual actuator for retracting and advancing a therapeutic working element of an intravascular catheter system according to the present invention comprises:

a hollow cylindrical bracing member including an open proximal end and a distal end;

a hollow cylindrical retracting member, the retracting member being slidable into the open proximal end of the bracing member, the retracting member having a proximal end;

an actuation shaft disposed axially within the retracting member and the bracing member;

at least one pulling wire, each of the at least one pulling wire having a proximate end anchored proximate the proximal end of the retracting member and a distal end secured to the therapeutic working element; and at least one resilient connecting member having a proximal end attached proximate the proximal end of the retracting member, and a distal end attached proximate the distal end of the bracing member, whereby a manually applied external force applied to the at least one resilient connecting member urges the retracting member in a proximal direction with respect to the bracing member, thereby pulling on the at least one pulling wire, and retracting and operating the therapeutic working element of the catheter system. In this exemplary embodiment, a proximal hub is fitted to the proximal end of the retracting member, and the proximal end of each of the at least one pulling wire is anchored within this proximal hub. In this exemplary embodiment, the pulling wire or wires is made of KEVLAR material, fiber composite material, or other high strength material susceptible to being woven or otherwise formed into thin wires.

An advantage of this exemplary embodiment is that the actuating shaft does not transmit the mechanical forces imparted to the resilient connecting members. Rather, in this exemplary embodiment, it is the pulling wires that transmit the force from the resilient connecting members and the retracting member to the therapeutic working element of the catheter system. This remedies problems encountered when the actuation shaft of the catheter system is unable to transmit the forces applied by the physician on the connecting members to the therapeutic working member.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein.

DETAILED DESCRIPTION OF THE INVENTION

Figure 1:
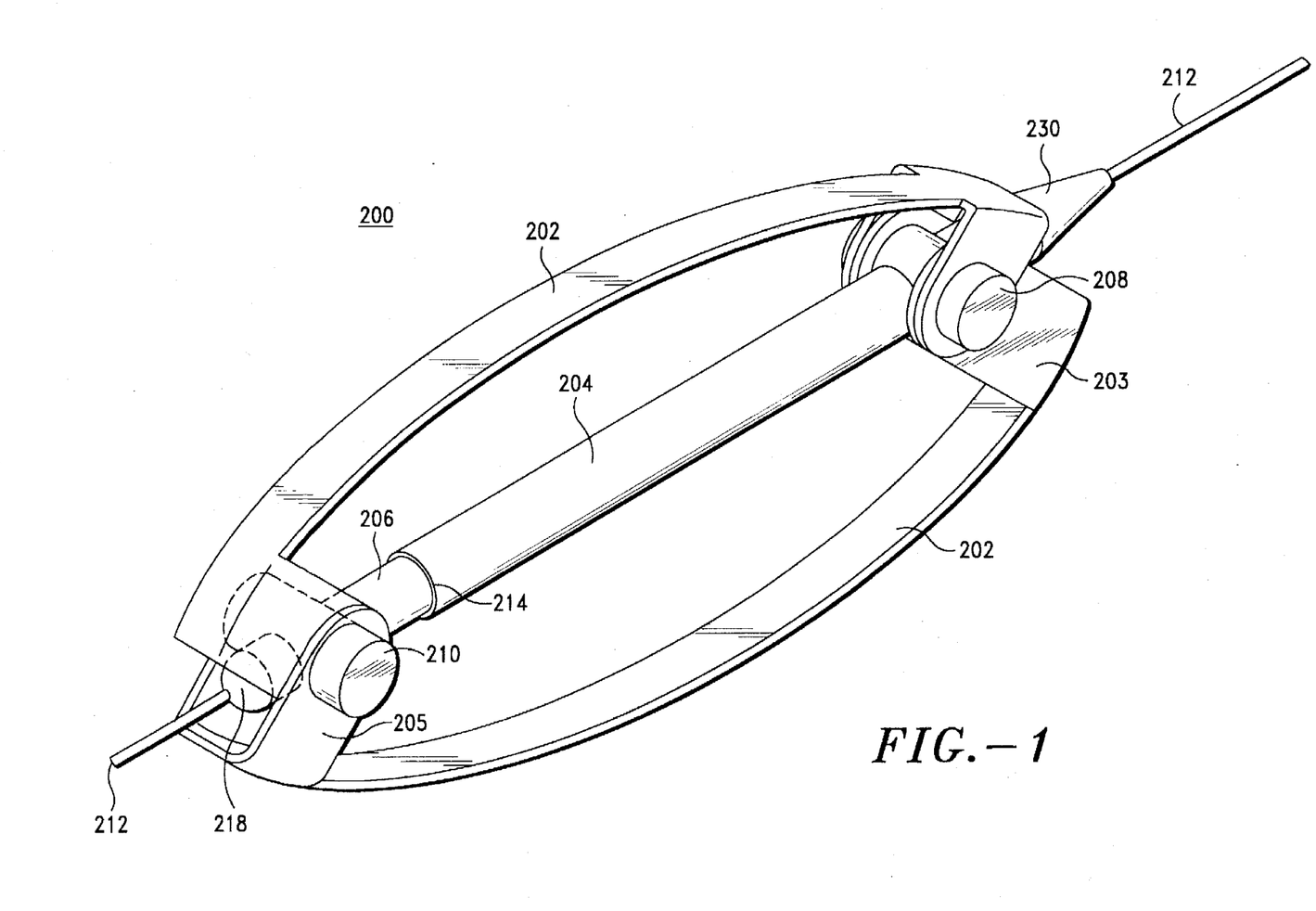
FIG. 1 illustrates an exemplary embodiment of a manual actuator for retracting and advancing an end member of an intravascular catheter according to the present invention.

The invention will be described particularly with reference to FIG. 1. FIG. 1 shows an exemplary embodiment of the manual actuator, shown generally at 200, for retracting and advancing, or operating, a therapeutic working element. The manual actuator, in operation, causes the retraction and advancement of the actuation shaft 212. The actuation shaft 212, by virtue of its reciprocating movement, may also operate a blunt end member, such as is disclosed in copending U.S. Application No. XX/XXX,XXX, attorney docket number LUMN1594, commonly assigned, the specification of which is included herewith by reference in its entirety. Of course, the manual actuator illustrated in FIG. 1 can be adapted to most any catheter apparatus whose therapeutic working element requires a low frequency, manually and selectively controlled reciprocating movement, and should not be construed as being limited to any particular type of the therapeutic working element.

Figure 4:
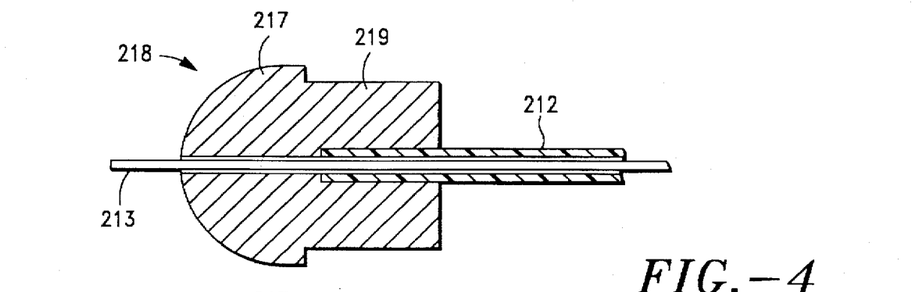
FIG. 4 is a cross sectional view of an exemplary embodiment of the proximal hub of the manual actuator according to the present invention.

The manual actuator 200 includes a hollow cylindrical retracting member 206 which has a proximal hub 218 attached to the proximal end thereof. FIG. 4 shows a cross sectional view of one embodiment of a proximal hub according to the present invention. As shown in FIG. 4, the proximal hub 218 has a cylindrical base portion 219 and an integral semi-hemispherical endcap 217. The cylindrical base portion 219 is dimensioned so as to fit snugly within the proximal open end of the hollow cylindrical retracting member 206. The proximate hub 218 includes an axial through bore for accommodating at least the actuation shaft of the catheter system. The actuation shaft 212, in the embodiment shown in FIG. 4, terminates and is secured within the through bore of the cylindrical base portion 219 of the proximal hub 218. A guidewire 213 is arranged within the actuation shaft 212 of the catheter device, and emerges at the proximal-most point of the semi-hemispherical endcap 217.

Figure 5:
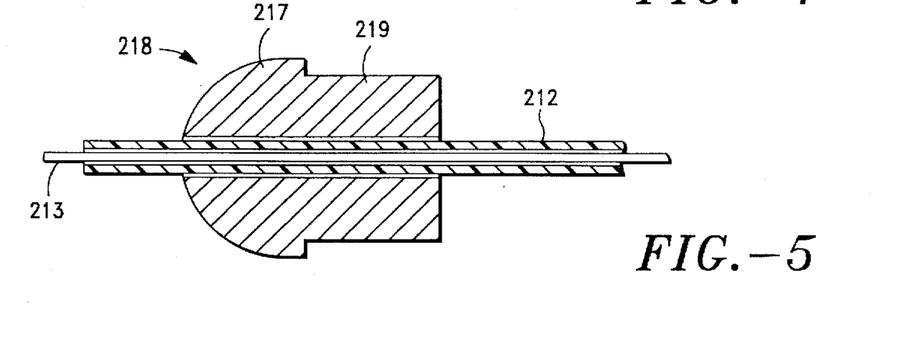
FIG. 5 is a cross sectional view of another exemplary embodiment of the proximal hub of the manual actuator according to the present invention.

FIG. 5 shows another exemplary embodiment of the proximal hub 218 according to the present invention. In FIG. 5, the actuation shaft 212 is not terminated within the axial through bore of the proximal hub 218, as it is in FIG. 4. Rather, in FIG. 5, the proximal hub 218 accommodates the actuation shaft 212 along its entire longitudinal axis. Indeed, in the embodiment shown in FIG. 5, the actuation shaft 212, emerges at the proximal-most point of the semi-hemispherical endcap 217. The actuation shaft 212, although traversing the entire length of the proximal hub 218 in the axial through bore thereof, is nevertheless secured thereto. In both FIGS. 4 and 5, the guidewire 213 can be seen within the actuation shaft 212.

Returning now to FIG. 1, the retracting member 206 is fitted within the open proximal end of a hollow cylindrical bracing member 204. The inner diameter of the hollow cylindrical bracing member 204 is slightly larger than the outer diameter of the retracting member 206, thereby allowing the retracting member 206 to fit and slide within the hollow cylindrical bracing member 204, through its open proximal end 214. In this fashion, the retracting member 206 and the bracing member 204 are free to slide against one another, in a telescoping fashion. The actuation shaft 212, as shown in FIGS. 4 and 5, is secured to the proximal hub 218. This permits mechanical force applied to the manual actuator 200 to be transmitted to the actuator shaft 212, via the proximal hub 218. The actuation shaft 212 is disposed within the manual actuator, along its longitudinal axis. A pair of bracing member mounting pins 208 is secured near the distal end of the bracing member 204, on its tubular outer surface. The two bracing member mounting pins 208 are disposed diametrically opposite relative to one another, so as to radially project from the bracing member 204. Alternatively, the pair of bracing member pins 208 may be unitarily and integrally formed, and secured proximal to the distal end of the bracing member 204. These unitarily and integrally formed bracing member pins 208 include a cylindrical opening therethrough, whose axis is orthogonal to the longitudinal axis of the pins 208 for snugly fitting the bracing member 204 therein. Similarly, a pair of retracting member mounting pins 210 is secured near the proximal end of the retracting member 206, on its tubular outer surface. The two retracting member mounting pins 210 are disposed diametrically opposite one another, so as to radially project from the retracting member 206. Alternatively, the pair of retracting member pins 210 may be unitarily and integrally formed, and secured near to the proximal end of the retracting member 206. These unitarily and integrally formed retracting member pins 210 include a cylindrical opening therethrough, whose axis is orthogonal to the longitudinal axis of the pins 210 for snugly fitting the retracting member 206 therein.

A pair of resilient connecting members 202 are mounted onto the bracing member mounting pins 208 and to the retracting member mounting pins 210. The connecting members 202 are made of thin strips of resilient material which regain their original shape after being deformed. One end of each of the connecting members 202 is pivotally connected onto the bracing member mounting pins 208, whereas the other end of each of the connecting members 202 is pivotally connected to the retracting member mounting pins 210. The resilient connecting members are mounted onto the mounting pins 208 and 210 in such a manner that, when unstressed by a manually applied external force, they exert a force in the distal direction on the retracting member 206 and a force in the proximal direction on the bracing member 204. Therefore, when unstressed by a manually applied external force, the connecting members 202 urge the retracting member 206 within the hollow interior of the bracing member 204.

Figure 2:
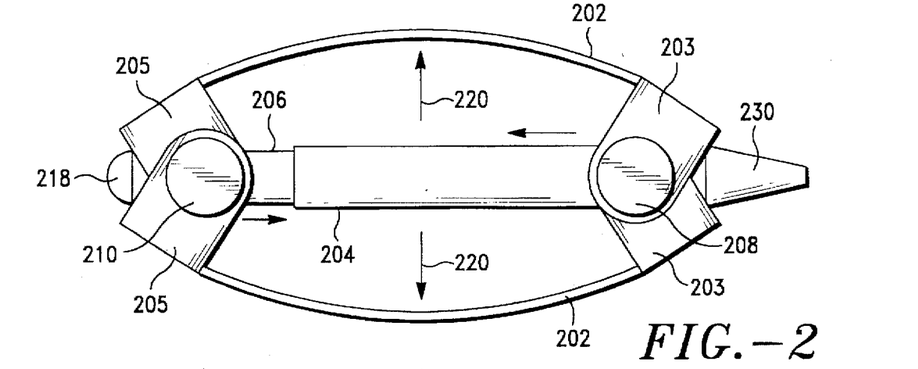
FIG. 2 illustrates the operation of the manual actuator of FIG. 1 when the resilient connecting members of the manual actuator are in their normal bias state.

FIG. 2 illustrates the forces that the connecting members 202 exert on the retracting member 206 and the bracing member 204. As shown in FIG. 2, the connecting members 202 act, in the absence of a manually applied external force, to exert an outward force in the direction of the arrows 220, that is, a direction which is toward and orthogonal to the bracing member 204 and the retracting member 206. In exerting the forces 220, the distal ends of the connecting members 202 pivot about the bracing member mounting pins 208, whereas the proximal ends of the connecting members 202 pivot about the retracting member mounting pins 210. In so doing, the compressive stresses applied to the resilient connecting members 202 upon mounting them to the mounting pins 208 and 210, urge the retracting member toward, and into the tubular interior hollow of the bracing member 204.

The distal ends of the connecting members 202 are pivotally mounted onto the bracing member mounting pins 208 by means of distal flanges 203 having an opening therethrough for pivotally fitting the bracing member mounting pins 210 therein. Similarly, the proximal ends of the connecting members 202 are pivotally mounted onto the retracting member mounting pins by means of proximal flanges 205 having an opening therethrough for pivotally fitting the retracting member mounting pins therein.

Figure 3:
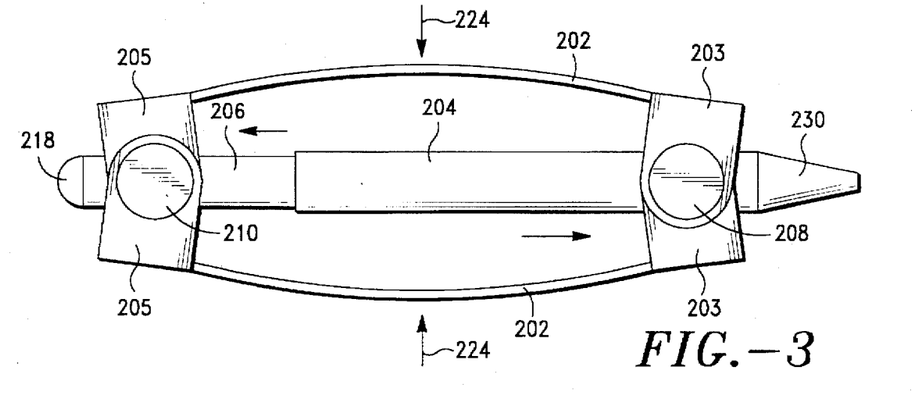
FIG. 3 illustrates the operation of the manual actuator of FIG. 1 when the resilient connecting members of the manual actuator are subjected to a force tending to bring them closer together.

As shown in FIG. 3, when a manually applied external force in the direction of arrows 224 is applied to the connecting members 202, the proximal ends of the connecting members 202 pivot about the retracting member mounting pins 210 and the distal ends of the connecting members 202 pivot about the bracing members mounting pins 208. As the connecting members 202 pivot about the mounting pins 208, 210, they urge the retracting member 206 in the proximal direction, away from the bracing member 204, thereby causing the distance between the bracing member mounting pins 208 and the retracting member mounting pins 210 to increase. This distance increases as the degree of curvature of the connecting members 202 decreases under the influence of the manually applied external force indicated by arrows 224. The mounting pins 208, 210 are at their greatest distance from one another when the degree of curvature of the connecting members 202 is at its lowest. That is, the retracting member 206 and thus the actuation shaft 212 are most retracted when the connecting members 202 are substantially parallel, under the action of the forces 224. When the manually applied external forces 224 are removed or decreased in magnitude, the connecting members 202 tend to return to their original shape, as shown in FIG. 2. Thus, the retracting member 206 advances the actuating shaft 212 which, in turn, causes the operation or the advancement of at least a portion of the therapeutic working member. The manual application of the external force 224 (FIG. 3), followed by its release (FIG. 4) corresponds to the physician squeezing the connecting members 202 in his or her hands, and releasing the applied squeezing force. It is this squeezing and releasing which causes the retracting member 206 to retract and advance, and causes the reciprocal motion of the actuating shaft 212 attached to the proximal hub 218 of the retracting member 206.

Figure 6:
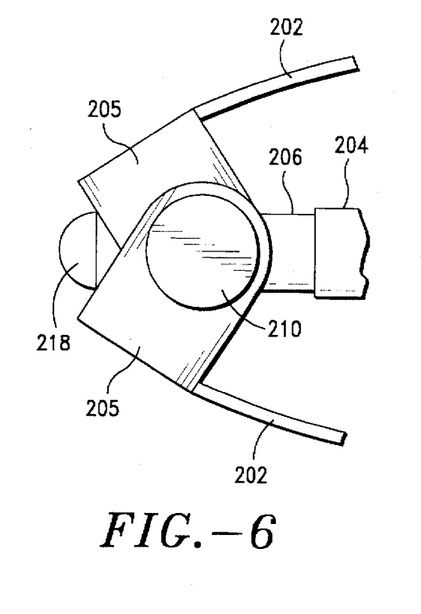
FIG. 6 is a fragmentary side view detail of the proximal end of the manual actuator according to the present invention.
Figure 7:
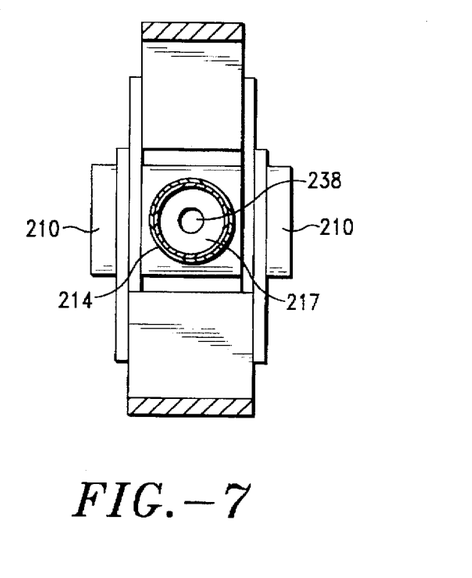
FIG. 7 is a front view of the proximal end of the manual actuator according to the present invention.

FIGS. 6 and 7 show side and front views, respectively, of the proximal end of the manual actuator 200 according to the present invention. As is readily apparent, the proximal hub 218 is fitted within the open proximal end of the retracting member 206. The connecting members 202 are pivotally attached to the retracting member mounting pins 210 via proximal flanges 205. This pivotal attachment allows the retracting member 206 to be retracted and advanced under the influence of external forces manually applied by a physician's hand. The front view of FIG. 7 shows the bracing member mounting pins 210 which radially project from the retracting member 206 at diametrically opposed positions relative to one another. As the retracting member 206 telescopes into the bracing member 204, the outline of the open proximal end of the bracing member 204 is visible in this view. The semi-hemispherical endcap 217 includes an opening 238 of its axial through bore for passage of the actuating shaft 212 and the guidewire 213, or just the guidewire 213.

Figure 8:
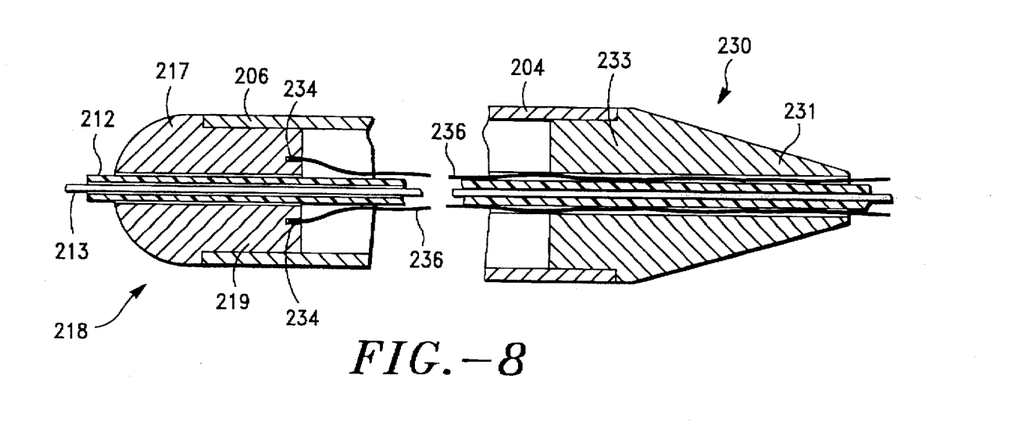
FIG. 8 is a cross sectional view of another exemplary embodiment of the manual actuator according to the present invention, showing the proximal hub, the distal hub and the pulling wires.

FIG. 8 shows a cross sectional view of both the proximal hub 218 and the distal hub 230. For clarity, the entire lengths of the retracting member 206 and the bracing member 204 are not shown in FIG. 8. The mounting pins 208 and 210, together with the connecting members 202 secured thereto, have also been omitted from FIG. 8, so as to clearly show the cross sections of the proximal and distal hubs 218 and 230. Proceeding from the left to the right, the proximal hub 218, in this exemplary embodiment, includes a cylindrical base portion 219 and an integral semi-hemispherical endcap 217. The cylindrical base portion 219 is dimensioned so as to fit snugly within the proximal open end of the hollow cylindrical retracting member 206. The proximal hub 218 includes a proximal hub through bore which accommodates the actuation shaft 212 along its entire length. Indeed, in this embodiment, the proximal endcap 218 is traversed along its entire length by the actuation shaft 212, which emerges at the proximal-most point of the semi- hemispherical endcap 217. The actuation shaft 212, although traversing the entire length of the proximal hub 218 within the proximal hub axial through bore, is nevertheless secured thereto. The actuation shaft also emerges from the distal-most point of the distal hub 230, through the distal hub axial through bore. The guidewire 213 is disposed within the actuation shaft 212, and emerges from the proximal end and the distal end of the proximal and distal hubs 218, 230, respectively. The distal hub 230, in this exemplary embodiment, includes a cylindrical base portion 233 and an integral conical endcap 231. The cylindrical base portion 233 is dimensioned so as to fit snugly within the distal open end of the hollow cylindrical bracing member 204. The distal hub 230 includes a distal hub through bore which accommodates the actuation shaft 212 along its entire length. Indeed, in this embodiment, the distal endcap 230 is traversed along its entire length by the actuation shaft 212, which emerges at the distal-most point of the integral conical endcap 231.

There are situations wherein it is not desirable to cause the actuation shaft of the catheter device to transmit the mechanical forces applied by the physician's hand on the connecting members 202 to the therapeutic working member. Indeed, an actuation shaft of long length may not efficiently transmit all of the forces applied to the connecting members, especially if the actuation shaft is made of a compressible or stretchable material. In that case, the force applied to the connecting members, and the retraction of the retracting member may be partially or totally taken up by any slack present in a long length of actuation shaft, or by its compression or stretching. For that reason, and in these situations, it is desirable to use another medium for transmitting the retraction and advancement of the retracting member 206 relative to the bracing member 204 to the actuation shaft 212.

That role is discharged, in the embodiment shown in FIG. 8, by one or more pulling wire 236. As shown in FIG. 8, the pulling wires 236 are anchored within the cylindrical base 219 of the proximal hub 218 at their proximal ends 234. The pulling wires 236 travels adjacent to the actuation shaft and terminates at and is secured to the therapeutic working element. The pulling wire 236 is made of any material exhibiting high tensile strength and which does not stretch or compress appreciably when tensioned. A suitable material for the pulling wires 236 is KEVLAR, due to its high strength and its ready susceptibility to being be woven or otherwise formed into thin strands. The pulling wire 236, and not the actuation shaft 212, in this embodiment, transmits the mechanical force from the retracting member 206 to the therapeutic working member. As the proximal end 234 of the pulling wire 236 is anchored within the cylindrical base 219 of the proximal hub 218, when the retracting member 206 retracts, the pulling wire is also pulled in the proximal direction and retracts at least a portion of, or operates the therapeutic working element of the catheter. The actuation shaft 212, in this manner, does not transmit the mechanical force to the working element. Thus the problems which can occur with long length actuation shafts, or compressible or stretchable actuation shafts, are solved through the use of the pulling wire 236. In the embodiment of FIG. 8, two pulling wires 236 are shown. Moreover, in FIG. 8, the actuation shaft 212 does not transmit any mechanical force to the working element, and the actuation shaft 212 is not secured within either the proximal or distal endcaps 218 and 230, respectively. It is to be understood that the proximate hub of FIG. 3 is equally compatible with the embodiment of the present invention depicted in FIG. 8. Moreover, any proximal hub which anchors the pulling wire or wires 236 thereto is equally compatible with the exemplary embodiment of FIG. 8, as those of skill in this art will readily recognize, and any manual actuator equipped with such proximal hubs should be deemed to fall within the scope of the present invention.

While the foregoing detailed description has described several embodiments of the present invention, it is to be understood that the above description is illustrative only and not limiting of the disclosed invention. Particularly, the invention need not be limited to resilient connecting members made of thin strips of resilient material. It will be appreciated that other connecting members could also be devised within the spirit and scope of this invention. For example, the resilient connecting member could be a rubber balloon connecting the distal end of the bracing member to the proximate end of the retracting member. It will also be appreciated that the shape of the various elements can vary from those described herein. For example, the shape of the proximate and distal hubs can vary without, however, departing from the spirit of the present invention. Thus, the invention is to be limited only by the claims as set forth below.

What is claimed is:

1. A manual actuator for retracting and advancing a therapeutic working element of an intravascular catheter system via an actuation shaft, the manual actuator comprising:
   a hollow cylindrical bracing member including an open proximal end and a distal end;
   a hollow cylindrical retracting member, the retracting member being slidable into the open proximal end of the bracing member, the retracting member having a proximal end;
   an actuation shaft, a proximal end of the actuation shaft being secured to the proximal end of the retracting member, a distal end of the actuation shaft being secured to the therapeutic working element, and
   at least one resilient connecting member having a proximal end attached proximate the proximal end of the retracting member, and a distal end attached proximate the distal end of the bracing member,
   whereby a manually applied external force applied to the at least one resilient connecting member urges the retracting member in a proximal direction with respect to the bracing member, thereby retracting the actuation shaft and operating the working element of the catheter system.

2. The manual actuator of claim 1, further comprising:
   a pair of bracing member mounting pins secured to the bracing member at a position proximate the distal end of the bracing member and projecting radially from the bracing member;
   a pair of retracting member mounting pins secured to the retracting member at a position proximate the proximal end of the retracting member and projecting radially from the retracting member;
   wherein the proximal end of each of the at least one connecting member is pivotally attached to a corresponding pin of the pair of retracting member mounting pins and the distal end of each of the at least one connecting member is pivotally attached to a corresponding pin of the pair of bracing member mounting pins.

3. The manual actuator of claim 2, wherein the pair of bracing member mounting pins is unitarily and integrally formed.

4. The manual actuator of claim 2, wherein the pair of retracting member mounting pins is unitarily and integrally formed.

5. The manual actuator of claim 1, wherein the proximal end of the hollow cylindrical retracting member is fitted with a proximal hub having an axial through bore for accommodating at least the actuation shaft along at least a portion of the longitudinal axis of the proximal hub.

6. The manual actuator of claim 1, wherein the proximal end of the hollow cylindrical retracting member is fitted with a proximal hub, the proximal hub having a first cylindrical base portion and an integral endcap, the cylindrical base portion and the endcap including an actuating shaft axial through bore dimensioned to accommodate at least an actuation shaft of the catheter system.

7. The manual actuator of claim 1, wherein the proximal end of the hollow cylindrical retracting member is fitted with a proximal hub, the proximal hub having a first cylindrical base portion and an integral endcap, the cylindrical base portion including an actuating shaft axial through bore dimensioned to accommodate at least the actuation shaft, the endcap including a guidewire axial through bore dimensioned to accommodate a guidewire of the catheter system, the guidewire axial through bore being aligned with the actuating shaft axial through bore.

8. The manual actuator of claim 1, further comprising a proximal hub fitted to the proximal end of the retracting member, the proximal end of the actuation shaft being anchored within the proximal hub.

9. The manual actuator of claim 8, wherein the proximal hub has a first cylindrical base portion and an integral endcap, the proximal end of the actuation shaft being anchored within the integral endcap.

10. The manual actuator of claim 1, wherein each of the at least one resilient connecting member is made of a thin strip of resilient material which regains its shape after being deformed.

11. The manual actuator of claim 1, wherein the distal end of the hollow cylindrical bracing member is fitted with a distal hub having an axial through bore for accommodating at least the actuation shaft.

12. A manual actuator for retracting and advancing a therapeutic working element of an intravascular catheter system, the manual actuator comprising:
   a hollow cylindrical bracing member including an open proximal end and a distal end;
   a hollow cylindrical retracting member, the retracting member being slidable into the open proximal end of the bracing member, the retracting member having a proximal end;
   an actuation shaft disposed axially within the retracting member and the bracing member;
   at least one pulling wire, the at least one pulling wire having a proximate end anchored proximate the proximate end of the retracting member and a distal end secured to the therapeutic working element; and
   at least one resilient connecting member having a proximal end attached proximate the proximal end of the retracting member, and a distal end attached proximate the distal end of the bracing member,
   whereby a manually applied external force applied to the at least one resilient connecting member urges the retracting member in a proximal direction with respect to the bracing member, thereby pulling on the at least one pulling wire, and retracting and operating the therapeutic working element of the catheter system.

13. The manual actuator of claim 12, further comprising:
   a pair of bracing member mounting pins secured to the bracing member at a position proximate the distal end of the bracing member and projecting radially from the bracing member;
   a pair of retracting member mounting pins secured to the retracting member at a position proximate the proximate end of the retracting member and projecting radially from the retracting member;
   wherein the proximal end of each of the at least one connecting member is pivotally attached to a corresponding pin of the pair of retracting member mounting pins and the distal end of each of the at least one connecting member is pivotally attached to a corresponding pin of the pair of bracing member mounting pins.

14. The manual actuator of claim 12, wherein the pair of bracing member mounting pins is unitarily and integrally formed.

15. The manual actuator of claim 12, wherein the pair of retracting member mounting pins is unitarily and integrally formed.

16. The manual actuator of claim 12, wherein the proximal end of the hollow cylindrical retracting member is fitted with a proximal hub having an axial through bore for accommodating at least the actuation shaft along at least a portion of the longitudinal axis of the proximal hub.

17. The manual actuator of claim 12, wherein the proximal end of the hollow cylindrical retracting member is fitted with a proximal hub, the proximal hub having a first cylindrical base portion and an integral endcap, the cylindrical base portion and the endcap including an actuating shaft axial through bore dimensioned to accommodate at least an actuation shaft of the catheter system.

18. The manual actuator of claim 12, wherein the proximal end of the hollow cylindrical retracting member is fitted with a proximal hub, the proximal hub having a first cylindrical base portion and an integral endcap, the cylindrical base portion including an actuating shaft axial through bore dimensioned to accommodate at least the actuation shaft, the endcap including a guidewire axial through bore dimensioned to accommodate a guidewire of the catheter system, the guidewire axial through bore being aligned with the actuating shaft axial through bore.

19. The manual actuator of claim 12, further comprising a proximal hub fitted to the proximal end of the retracting member, the proximal end of each of the at least one pulling wire being anchored within the proximal hub.

20. The manual actuator of claim 19, wherein the proximal hub has a first cylindrical base portion and an integral endcap, the proximal end of each of the at least one pulling wire being anchored within the integral endcap.

21. The manual actuator of claim 12, wherein each of the at least one resilient connecting member is made of a thin strip of resilient material which regains its shape after being deformed.

22. The manual actuator of claim 12, wherein the distal end of the hollow cylindrical bracing member is fitted with a distal hub having an axial through bore for accommodating at least the actuation shaft.

23. The manual actuator of claim 12, wherein the at least one pulling wire is made of KEVLAR material.

24. A manual actuator for retracting and advancing a therapeutic working element of an intravascular catheter system via an actuation shaft, the manual actuator comprising:

a hollow cylindrical bracing member including an open proximal end and a distal end;

a hollow cylindrical retracting member, the retracting member being slidable into the open proximal end of the bracing member, the retracting member having a proximal end;

an actuation shaft, a proximal end of the actuation shaft being secured proximal to the proximal end of the retracting member, a distal end of the actuation shaft being secured to the therapeutic working element, and a pair resilient connecting members, each connecting member of the pair having a proximal end pivotally attached to the retracting member proximate its proximate end, and a distal end pivotally attached to the bracing member proximate its distal end, whereby a manually applied external squeezing force applied to the pair of resilient connecting member urges the retracting member in a proximal direction with respect to the bracing member, thereby retracting the actuation shaft and operating the working element of the catheter system.

25. The manual actuator of claim 24, further comprising:

a pair of bracing member mounting pins secured to the bracing member at a position proximate the distal end of the bracing member and projecting radially from the bracing member;

a pair of retracting member mounting pins secured to the retracting member at a position proximate the proximate end of the retracting member and projecting radially from the retracting member;

wherein the proximal end of each connecting member of the pair of connecting members is pivotally attached to a corresponding pin of the pair of retracting member mounting pins and the distal end of each of the connecting members of the pair of connecting members is pivotally attached to a corresponding pin of the pair of bracing member mounting pins.

26. The manual actuator of claim 25, wherein the pair of bracing member mounting pins is unitarily and integrally formed.

27. The manual actuator of claim 25, wherein the pair of retracting member mounting pins is unitarily and integrally formed.

28. The manual actuator of claim 24, wherein the proximal end of the hollow cylindrical retracting member is fitted with a proximal hub having an axial through bore for accommodating at least the actuation shaft along at least a portion of the longitudinal axis of the proximal hub.

29. The manual actuator of claim 24, wherein the proximal end of the hollow cylindrical retracting member is fitted with a proximal hub, the proximal hub having a first cylindrical base portion and an integral endcap, the cylindrical base portion and the endcap including an actuating shaft axial through bore dimensioned to accommodate at least an actuation shaft of the catheter system.

30. The manual actuator of claim 24, wherein the proximal end of the hollow cylindrical retracting member is fitted with a proximal hub, the proximal hub having a first cylindrical base portion and an integral endcap, the cylindrical base portion including an actuating shaft axial through bore dimensioned to accommodate at least the actuation shaft, the endcap including a guidewire axial through bore dimensioned to accommodate a guidewire of the catheter system, the guidewire axial through bore being aligned with the actuating shaft axial through bore.

31. The manual actuator of claim 24, further comprising a proximal hub fitted to the proximal end of the retracting member, the proximal end of the actuation shaft being anchored within the proximal hub.

32. The manual actuator of claim 30, wherein the proximal hub has a first cylindrical base portion and an integral endcap, the proximal end of the actuation shaft being anchored within the integral endcap.

33. The manual actuator of claim 24, wherein each connecting member of the pair of connecting members is made of a thin strip of resilient material which regains its shape after being deformed.

34. The manual actuator of claim 24, wherein the distal end of the hollow cylindrical bracing member is fitted with a distal hub having an axial through bore for accommodating at least the actuation shaft.

* * * * *